US008547544B2

United States Patent
Horikoshi et al.

(10) Patent No.: US 8,547,544 B2
(45) Date of Patent: Oct. 1, 2013

(54) MULTICHANNEL PHOTOMETRIC MEASUREMENT APPARATUS

(75) Inventors: Kumiko Horikoshi, Tokyo (JP); Yasushi Ichizawa, Tokyo (JP); Shigeyuki Kakuta, Tokyo (JP); Kazufumi Nishida, Tokyo (JP)

(73) Assignee: Yokogawa Electric Corporation, Musashino-shi, Tokyo (JP)

( * ) Notice: Subject to any disclaimer, the term of this patent is extended or adjusted under 35 U.S.C. 154(b) by 162 days.

(21) Appl. No.: 13/186,967

(22) Filed: Jul. 20, 2011

(65) Prior Publication Data

US 2012/0019815 A1    Jan. 26, 2012

(30) Foreign Application Priority Data

Jul. 20, 2010   (JP) ................... 2010-162619

(51) Int. Cl.
  *G01J 1/34*  (2006.01)
  *G01J 3/50*  (2006.01)
(52) U.S. Cl.
  USPC ............. 356/217; 356/319; 356/326
(58) Field of Classification Search
  USPC ............ 356/213–217, 39–41, 463, 317, 319, 356/326; 600/322, 323, 327; 250/494.1, 250/493.1
  See application file for complete search history.

(56) References Cited

U.S. PATENT DOCUMENTS

| | | | | |
|---|---|---|---|---|
| 4,800,885 | A * | 1/1989 | Johnson | 600/330 |
| 5,315,993 | A * | 5/1994 | Alcala | 600/341 |
| 5,349,952 | A * | 9/1994 | McCarthy et al. | 600/473 |
| 5,830,137 | A * | 11/1998 | Scharf | 600/323 |
| 6,370,408 | B1 * | 4/2002 | Merchant et al. | 600/322 |
| 6,778,923 | B2 * | 8/2004 | Norris et al. | 702/74 |
| 8,049,892 | B2 * | 11/2011 | Shakespeare et al. | 356/406 |
| 8,314,388 | B2 * | 11/2012 | Tixier et al. | 250/338.1 |
| 2002/0068859 | A1 * | 6/2002 | Knopp | 600/322 |
| 2004/0260520 | A1 * | 12/2004 | Braendle et al. | 702/189 |
| 2006/0092328 | A1 * | 5/2006 | Anderson et al. | 348/571 |
| 2009/0027655 | A1 * | 1/2009 | Haran | 356/51 |
| 2009/0111191 | A1 * | 4/2009 | Bonne et al. | 436/164 |
| 2010/0245834 | A1 * | 9/2010 | Strandjord | 356/463 |

FOREIGN PATENT DOCUMENTS

JP   2008-539422 A   11/2008

* cited by examiner

*Primary Examiner* — Sang Nguyen
(74) *Attorney, Agent, or Firm* — Westerman, Hattori, Daniels & Adrian, LLP

(57) ABSTRACT

A multichannel photometric measurement apparatus according to one embodiment includes: a single signal generator for generating an initial signal, the initial signal containing a harmonic component for collectively generating a plurality of modulation signals; a light emitting device including a plurality of light sources that are respectively drivable by each of the plurality of modulation signals having different frequencies; a light detector for detecting a plurality of kinds of light emitted from the light emitting device; and discriminating means for discriminating a detected signal output from the light detector per frequency domain of each of the different frequencies for each of the modulation signals.

3 Claims, 7 Drawing Sheets

DUTY RATIO 50%

US 8,547,544 B2

MULTICHANNEL PHOTOMETRIC MEASUREMENT APPARATUS

CROSS-REFERENCE TO RELATED APPLICATION

This application is based on Japanese Patent Application No. 2010-162619 filed with the Japan Patent Office on Jul. 20, 2010, the entire content of which is hereby incorporated by reference.

BACKGROUND

1. Technical Field

Embodiments described herein relate to a multichannel photometric measurement apparatus, for example, a detecting portion of a measurement sensor for measuring the moisture percentage or thickness of a sheet (paper) using near infrared rays.

2. Related Art

In a process for manufacturing paper, it is important to control the moisture percentage of paper. This process thus requires a moisture measurement sensor which monitors the moisture content of paper being manufactured.

Examples of the method for measuring the moisture content include a method for calculating the moisture percentage by multivariable analysis of measurement results of transmission attenuation ratios obtained using near infrared rays.

Specifically, the moisture percentage is calculated from (1) the transmission attenuation ratio of 1.94-μm wavelength light, which is significantly absorbed into water, (2) the transmission attenuation ratio of 2.1-μm wavelength light, which is significantly absorbed into cellulose constituting 80% of paper, and (3) the transmission attenuation ratio of 1.7-μm wavelength light, which is absorbed into neither water nor cellulose.

A halogen lamp is used as a light source in many cases. Light emitted from the light source passes through paper. The transmitted light is detected by an InGaAs photodiode or a PbS cell sensitive to a wavelength band of the transmitted light.

FIG. 6A illustrates an example of a photometric measurement apparatus in the related art. In this apparatus, an upper sensor head 1 and a lower sensor head 2 are reciprocally driven in the direction of arrow X in synchronization with each other while being engaged with an O-shaped frame 3. A target to be measured (paper sheet) 4 is conveyed between the upper sensor head 1 and the lower sensor head 2 by a conveying unit (not illustrated), for example, in a direction coming out of the plane of the paper of the drawing. As a result, the upper sensor head 1 and the lower sensor head 2 scan the paper sheet in a zigzag manner. Note that the paper sheet 4 being conveyed is not in contact with the upper sensor head 1 or the lower sensor head 2.

FIG. 6B illustrates the upper sensor head 1 and the lower sensor head 2 in detail. In the example illustrated in FIG. 6B, a halogen lamp 5 and a filter wheel 6 are arranged in the upper sensor head 1. A pair of reflection mirrors 8 is arranged with the paper sheet 4 sandwiched therebetween. Three kinds of light having wavelengths of 1.94 μm, 2.1 μm, and 1.7 μm, respectively, are filtered through the filter wheel 6 and then becomes incident on the reflection mirrors 8.

After that, the three kinds of light are scattered by the pair of reflection mirrors, becomes incident on a light receiving element 10 and then converted into detected signals (electric signals). These detected signals are amplified by an amplifier 12 and A/D converted. After that, a CPU 11 calculates the moisture percentage of the paper sheet 4 based on the detected signals.

Recently, a method using a semiconductor light emitting element such as an LD or LED as a light source has been used in part of the industry (see FIG. 3 of JP-T-2008-539422 "SENSOR AND METHOD FOR MEASURING SELECTED COMPONENTS IN MOVING SHEET PRODUCTS"). In comparison with a halogen lamp, the LD and LED have a longer life and a higher luminous efficiency with respect to power consumption, and can be electrically modulated using a lock-in amplifier having a high noise canceling performance.

The semiconductor light emitting element can be electrically modulated unlike the halogen lamp light source that requires a mechanical scheme for modulation. The mechanical modulation may lead to, for example, developing a failure due to wear of a portion that moves mechanically and may involve an increase in cost incurred for a mechanism used to measure a modulation frequency. Furthermore, mechanical modulation is difficult at high frequencies. Electrical modulation, on the other hand, does not develop a failure due to wear. Electrical modulation also makes it possible to find out the frequency directly based on a drive frequency. Accordingly, a mechanism to measure the frequency may be spared.

FIG. 7 illustrates another example of the related art described in JP-T-2008-539422. FIG. 7 is a schematic diagram illustrating a moisture sensor system which measures moisture content in a moving paper sheet. This system includes a measurement wavelength light source controller 42 and a reference wavelength light source controller 40. The controller 42 modulates, and controls the temperature of, a measurement light source 16. The controller 40 modulates, and controls the temperature of, a reference light source 14.

A power source 41 is connected to the controllers 40 and 42. The light sources 14 and 16 are coupled to first ends of optical fibers 23 and 24, respectively. Second ends of the optical fibers 23 and 24 are connected to an optical head 28.

A sheet (paper) 30 is arranged adjacent to the optical head 28, so that light 31 can be directed from the optical head 28 to the sheet 30.

Part of reflected light 33 is condensed by the optical head 28. The optical head 28 delivers the condensed light to a detector 34 through an optical fiber 32. In this manner, the optical fibers 23 and 24 carry the beams from the light sources 14 and 16 to the optical head 28, respectively. The optical fiber 32, on the other hand, carries the beam from the detector.

This system includes an amplifier 36, a reference wavelength lock-in amplifier 20, a measurement wavelength lock-in amplifier 18, and a computer 19 for analyzing data signals. The amplifier 36 converts photoinduced current from the detector 34 into a voltage signal and inputs the voltage signal to the measurement wavelength lock-in amplifier 18 and the reference wavelength lock-in amplifier 20. The lock-in amplifiers 18 and 20 amplify the modulated signal while converting the signal into a DC-level signal. The lock-in amplifiers 18 and 20 further pass the converted signal through a low-pass filter (not illustrated), whereby unmodulated background noise is suppressed. As a result, a low-level modulated signal is eliminated from the background.

A cutoff frequency of the low-pass filter is ten times lower than the modulation frequency. The larger the difference between the cutoff frequency and the modulation frequency, the better the noise canceling performance of the lock-in detection. Waveforms output from internal oscillators of the lock-in amplifiers 18 and 20 are used as reference waveforms for the light source controllers 40 and 42 to modulate light output from the light sources 14 and 16.

The light from the reference light source 14 and the measurement light source 16 is transmitted through the common optical fibers 23 and 24 by frequency-division multiplexing (FDM). Consequently, a multiplexer and a demultiplexer can be configured. To perform FDM, the measurement light source 14 and the reference light source 16 are modulated at different frequencies by the controllers 40 and 42, respectively.

Multiplexing allows each light source to be modulated at a different frequency. A single set of the detector 34 and the preamplifier 36, therefore, has only to be provided to detect the wavelength of light emitted from each light source.

The sensor system illustrated in FIG. 7 detects light beams reflected from the sheet (paper) 30 in a reflective mode. In addition, a detector 29 may be arranged on the opposite side of the sheet 30 to detect light beams having passed through the sheet 30. This enables the system to detect the light beams also in a transmissive mode, in which case optical elements of the detector 29 are connected to the optical fiber 32.

With this method, light output from a plurality of semiconductor light emitting elements can be measured with one detector. This is because it is possible to modulate each light emitting element at a different frequency and to separate a detected signal from each light emitting element by discriminating the frequency of a light receiving signal. When using a light source such as a halogen lamp which outputs white light, on the other hand, it is necessary to resolve the wavelength of detected light using, for example, an optical filter. Therefore, one detector is needed for each filter, leading to an increase in cost and a complicated configuration of the optical system.

SUMMARY

A multichannel photometric measurement apparatus according to one embodiment includes: a single signal generator for generating an initial signal, the initial signal containing a harmonic component for collectively generating a plurality of modulation signals; a light emitting device including a plurality of light sources that are respectively drivable by each of the plurality of modulation signals having different frequencies; a light detector for detecting a plurality of kinds of light emitted from the light emitting device; and discriminating means for discriminating a detected signal output from the light detector per frequency domain of each of the different frequencies for each of the modulation signals.

DESCRIPTION OF EMBODIMENTS

Figure 1:
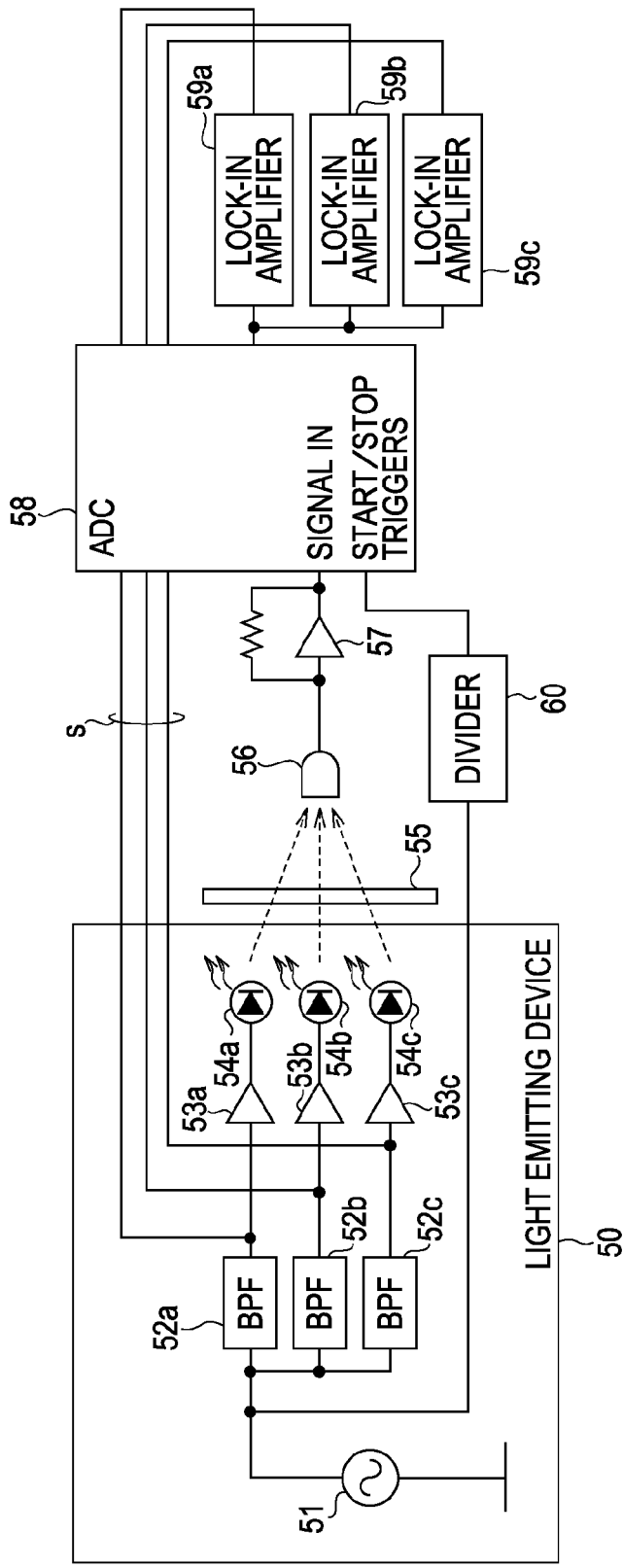
FIG. 1 is a block configuration diagram illustrating one embodiment of a multichannel photometric measurement apparatus.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically illustrated in order to simplify the drawing.

When detecting light output from a plurality of semiconductor light emitting elements with one detector, it is important to select an appropriate frequency for driving the elements. A detected signal is divided according to the number of elements. The divided signals are discriminated upon being passed through a bandpass filter (BPF) that employs, as a central frequency, a modulation frequency input to the elements. In this manner, the detected signal having a plurality of frequency components becomes a plurality of signals (discriminated signals) belonging to different frequency domains. In this case, the frequencies of the discriminated signals in each channel, when (partially) overlapped with each other, result in detection of noise. The frequency of the discriminated signal broadens since the time to load the detected signal output from the detector is finite. As a result, the above-described noise may be detected.

An object to be achieved by the multichannel photometric measurement apparatus is to generate a plurality of discriminated signals having no overlapped frequencies by discriminating a detected signal. For this purpose, electric signals are caused to have an orthogonal relationship with each other within the duration of loading the detected signal. This makes it possible to provide a multichannel photometric measurement apparatus free from noise. Discriminating means for discriminating a detected signal output from the light detector per frequency domain includes an A/D converter and lock-in amplifiers. As an alternative for the lock-in amplifiers, the discriminating means also includes a discrete Fourier transform (FFT). The lock-in amplifiers receive detected signals from the light detector that are made orthogonal with each other by an A/D converter, as well as references signals from bandpass filters that are orthogonal with each other. The FFT filters the detected signals from the light detector per frequency domain.

A multichannel photometric measurement apparatus according to a first aspect of the present embodiment includes: a single signal generator for generating an initial signal, the initial signal containing a harmonic component for collectively generating a plurality of modulation signals; a light emitting device including a plurality of light sources that are respectively drivable by each of the plurality of modulation signals having different frequencies; a light detector for detecting a plurality of kinds of light emitted from the light emitting device; and discriminating means for discriminating a detected signal output from the light detector per frequency domain of each of the different frequencies for each of the modulation signals.

A second aspect of the present embodiment is the multichannel photometric measurement apparatus according to the first aspect, wherein the light emitting device includes: the signal generator; and a plurality of bandpass filters each configured to extract a predetermined different frequency component from the initial signal generated by the signal generator, and the plurality of light sources is each drivable by a modulation signal having the frequency component extracted by corresponding one of the bandpass filters.

A third aspect of the present embodiment is the multichannel photometric measurement apparatus according to the first or second aspect, wherein the discriminating means includes an A/D converter that matches a width of a time window to load the detected signal with an integral multiple of an inverse of the frequency of the modulation signal to cause a plurality of frequency components contained in the detected signal input to the discriminating means to have an orthogonal relationship with each other.

A fourth aspect of the present embodiment is the multichannel photometric measurement apparatus according to the first or second aspect, wherein the signal generator is a rectangular wave generator for collectively generating the initial signals as a frequency comb having a predetermined frequency interval.

A fifth aspect of the present embodiment is the multichannel photometric measurement apparatus according to the second aspect, wherein each of the plurality of bandpass filters has a cutoff characteristic to respectively extract the predetermined different frequency component from the initial signal generated by the signal generator.

According to the first to fifth aspects, the plurality of frequency components contained in the detected signal has the orthogonal relationship within the duration of loading the detected signal. This makes it possible to discriminate the detected signal containing the plurality of frequency components into a plurality of discriminated signals having no overlapped frequencies.

In addition, signal generators that are the same in number as the plurality of light sources do not have to be provided. Therefore, the configuration of the apparatus can be simplified, leading to cost reduction.

FIG. 1 is a block configuration diagram illustrating a multichannel photometric measurement apparatus (the present measurement apparatus) according to the present embodiment.

The present measurement apparatus is for measuring the moisture percentage or thickness of a sheet (paper) 55. As illustrated in FIG. 1, the present measurement apparatus includes a light emitting device 50, a light detecting element 56, a current/voltage converter 57, an A/D converter (ADC) 58, lock-in amplifiers 59a, 59b and 59c, and a divider 60.

The light emitting device 50 includes a signal generator (light source driving device, or frequency generator), and a plurality of light sources. The signal generator generates a plurality of initial signals, each containing different frequency components, for driving the plurality of light sources. The plurality of light sources is driven by a plurality of modulation signals each having a different frequency component extracted from the initial signal.

The sheet (paper; sample) 55 is arranged between, and with a predetermined distance from, the light detecting element 56 of the light emitting device 50 and light sources 54a to 54c.

The light detecting element 56 detects light emitted from the light sources 54a to 54c and having passed through the sheet 55. The light detecting element 56 outputs a current signal corresponding to the detection result to the current/voltage converter 57.

The current/voltage converter 57 converts the input current signal into a voltage signal.

The voltage signal is then input to the A/D converter 58. Output signals (reference signals) from BPFs 52a to 52c of the light emitting device 50 are also input to the A/D converter 58.

The A/D converter 58 converts the input signals into digital signals.

Through the above process, the digital detected signals corresponding to the detection result obtained by the light detecting element 56 are generated. The detected signals are input to the lock-in amplifiers 59a to 59c. The above-described reference signals are also input to the lock-in amplifiers 59a to 59c.

The lock-in amplifiers 59a to 59c generate a plurality of signals (discriminated signals) belonging to different frequency domains by discriminating the input detected signals per frequency domain. The generation of the discriminated signal by the lock-in amplifier is described in detail later.

These discriminated signals are input to a CPU (not illustrated). The CPU calculates the moisture percentage and/or thickness of the sheet 55 based on the input discriminated signals.

The configuration of the light emitting device 50 is described in detail below.

The light emitting device 50 includes the signal generator 51 (rectangular wave generator), the three bandpass filters (hereinafter referred to as "BPFs") 52a, 52b and 52c, three light source driving amplifiers 53a, 53b and 53c, and the three light sources 54a, 54b and 54c. The BPFs 52a to 52c are connected to the signal generator 51. The light source driving amplifiers 53a to 53c amplify outputs from the BPFs 52a to 52c, respectively. The light sources 54a to 54c are configured by LDs (laser diodes) or LEDs (light emitting diodes).

The signal generator 51 generates a plurality of initial signals, each containing different frequency components, for driving the light sources 54a to 54c. Note that the different frequency components contained in each initial signal each have a value of integral multiple of any one frequency.

Figure 2A:
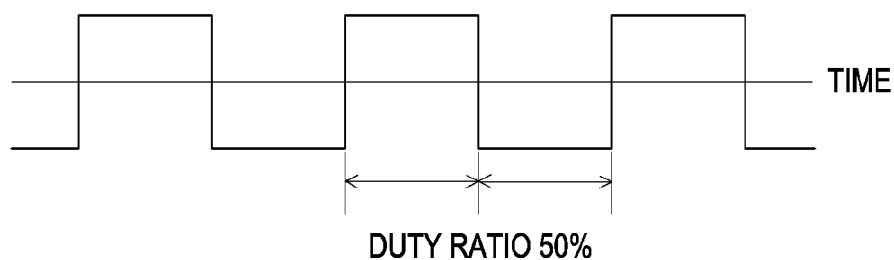
FIGS. 2A and 2B are partially enlarged views each illustrating a specific example of the apparatus of FIG. 1.
Figure 2B:
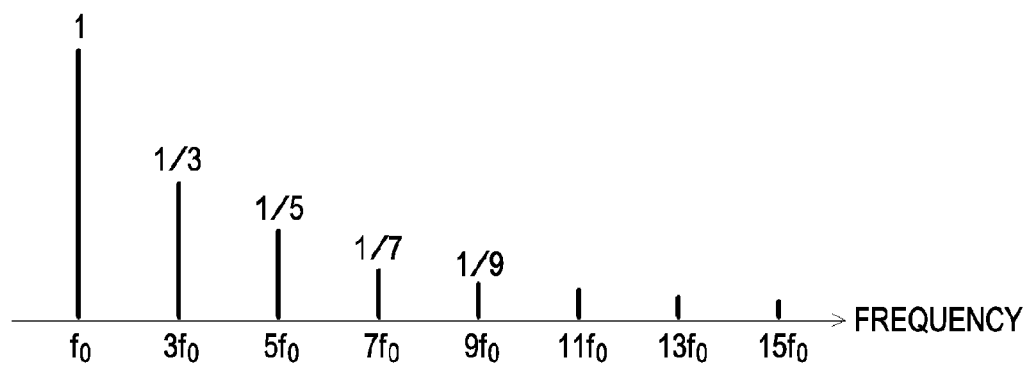

FIGS. 2A and 2B each illustrate an example of the initial signal generated by the signal generator 51. FIG. 2B illustrates a frequency comb obtained by performing Fourier transform on a rectangular wave output with a duty ratio of 50% illustrated in FIG. 2A. When using a single rectangular wave generator as the signal generator 51, harmonics of a rectangular wave may be utilized. By so doing, initial signals each containing a plurality of needed frequency components can be collectively generated as a frequency comb with predetermined frequency intervals.

Figure 3:
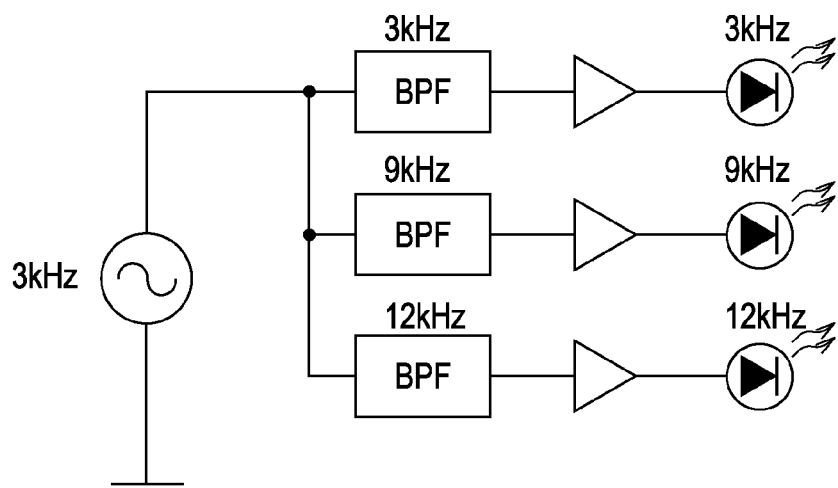
FIG. 3 is an explanatory diagram of a signal generator.

FIG. 3 is an explanatory diagram of the process for generating a modulation signal from the initial signal. The initial signal (e.g., a signal of 3 kHz containing harmonics) output from the signal generator 51 is divided by the same number as that of light sources. The divided initial signals are input to the BPFs 52a to 52c. The BPFs 52a to 52c each extract a specific frequency component from the initial signal. For example, the BPFs 52a to 52c extract frequency components of 3 kHz, 9 kHz, and 12 kHz, respectively. The BPFs 52a to 52c then generate modulation signals each having the extracted frequency component. In this manner, the BPFs 52a to 52c generate modulation signals of a sine wave having a specific frequency and extracted from the signal containing harmonics, that is, modulation signals each having a different frequency component.

Consequently, the light sources 54a to 54c are driven by the three modulation signals having different frequencies each having a value of integral multiple of any one frequency. The light sources 54a to 54c emit light having the same frequency as the input modulation signal to the sheet 55. The three kinds of light having passed through the sheet are then detected by the one light detecting element 56.

Therefore, the digital detected signal output through the light detecting element 56, the current/voltage converter 57, and the ADC 58 has three different frequency components corresponding to the three modulation signals. The digital detected signals are input to the lock-in amplifiers 59a to 59c.

The function of the lock-in amplifiers 59a to 59c is described in detail below.

The digital detected signal and one of the output signals (reference signals) from the BPFs 52a to 52c are input to each of the lock-in amplifiers 59a to 59c.

The lock-in amplifiers 59a to 59c compute an average or cumulative value of the results obtained by multiplying the two or more input signals within a certain time range. This computation is substantially the same in meaning as the computation of an inner product of the signals.

In this case, the reference signals input to the lock-in amplifiers 59a to 59c may have an orthogonal relationship with each other.

The orthogonal relationship is one in which the inner product becomes zero. This relationship can be expressed by the following equation:

$$\int_{-\pi}^{\pi} f(x) \cdot g(x) dx = 0 \quad (1)$$

A rectangular wave signal having a frequency lf and a rectangular wave signal having a frequency mf ($1 \neq m$) have the orthogonal relationship when the signals are in phase and the loading time is an integral multiple of 1/f (where l, m, and n are natural numbers).

As described above, the reference signals input to the lock-in amplifiers 59a to 59c from the BPFs 52a to 52c are sine waves having specific frequencies and extracted from the signals containing harmonics. The detected signals input to the lock-in amplifiers 59a to 59c from the ADC 58 are sine waves each having the three frequency components corresponding to the respective modulation signals (reference signals).

Therefore, when the signals input to each of the lock-in amplifiers 59a to 59c are in phase and the loading time is an integral multiple of 1/f (the integration range is from 0 to an), the equation (1) can be expressed as the following equations (2) and (3), where n, m, and l are natural numbers:

$$\int_0^{n\pi} \sin(mt) \cdot \sin(lt) dt = 0 \ (m \neq l) \quad (2)$$

$$\int_0^{n\pi} \sin(mt) \cdot \sin(lt) dt = 1 \ (m = l) \quad (3)$$

As is evident from these equations (2) and (3), when the signals having the orthogonal relationship are input to each lock-in amplifier, the value of 0 is output. When the signals having the same frequency are input, on the other hand, an average or cumulative value of the signals is simply output. Therefore, since one reference signal is input to each lock-in amplifier, only a discriminated signal having the same frequency as the input reference signal can be extracted from the detected signal.

In the above example, the reference signal (3 kHz) and the two frequency components (9 kHz and 12 kHz) out of the three frequency components of the detected signal have the orthogonal relationship. Therefore, only a discriminated signal of 3 kHz is output from the lock-in amplifier 59a, whereas discriminated signals of 9 kHz and 12 kHz are not output therefrom. Also, the reference signal (9 kHz) and the two frequency components (3 kHz and 12 kHz) out of the frequency components of the detected signal have the orthogonal relationship. Therefore, only the discriminated signal of 9 kHz is output from the lock-in amplifier 59b, whereas the discriminated signals of 3 kHz and 12 kHz are not output therefrom.

On the other hand, when two signals not orthogonal to each other are input to each lock-in amplifier, that is, when neither m nor l is an integer and m is not equal to l in the equations (2) and (3), the integration value is 0 to 1. The integration value comes closer to 0 as the range of integration time becomes longer. However, the measurement time is finite, and thus the integration value results in a certain value other than 0. That is, when the respective drive frequencies for the light sources 54a to 54c do not have the orthogonal relationship with each other, noise will be detected.

Note that when the two signals input to each lock-in amplifier are not in phase, these signals cannot be said to have the orthogonal relationship. In this case, the output (computation result given by the equation (1)) of the lock-in amplifier does not result in 0. Therefore, the present apparatus uses the single signal generator 51 for generating a plurality of initial signals each containing different frequency components. This configuration makes it possible to match the phases of the reference signals and detected signals, which are generated based on the initial signals and input to the lock-in amplifiers. In addition, the present measurement apparatus may include a mechanism for adjusting the phase. Alternatively, a biphase lock-in amplifier which uses both a sin component and a cos component as reference signals may also be used. In the latter case, adjustment of the phases of two signals may be skipped, which is efficient.

In the equations (1) and (2), it is important to select an appropriate integration range (corresponding to the range of loading time). As can be seen from the equations (1) and (2), the integration range is from 0 to nπ. When the integration range is outside of the above range (that is, when n is not a natural number), the output value is not 0. In this case, sin (mt) and sin (10 cannot be said to have the orthogonal relationship.

In this respect, the A/D converter (analog-to-digital converter) 58 has a function of matching the duration of a loaded waveform with an integral multiple of the period of a rectangular wave generated by the rectangular wave generator 51. With this function, the reference signals can mutually have the orthogonal relationship with each other.

Note that the frequency is generally determined (selected) in consideration of the measurement time (time resolution).

An operation of detecting moisture contained in paper by the present measurement apparatus is described next.

To detect the moisture contained in paper, the three light sources 54a to 54c are driven by three modulation signals having wavelengths of 1.94 μm, 2.1 μm, and 1.7 μm, respectively.

As illustrated in FIG. 1, light emitted from the light sources 54a to 54c passes through the target to be measured (paper) 55, is incident on the light detecting element 56, and is then converted into electric signals (detected signals). These detected signals are AC signals corresponding to the respective modulation frequencies for the light sources 54a to 54c. The detected signals, when they are, for example, current signals, are converted into voltage signals by the current/voltage converter 57. The detected signals are then converted into digital detected signals by the A/D converter 58 after being subjected to, for example, amplification by an amplifier (not illustrated) or the like.

Figure 4:
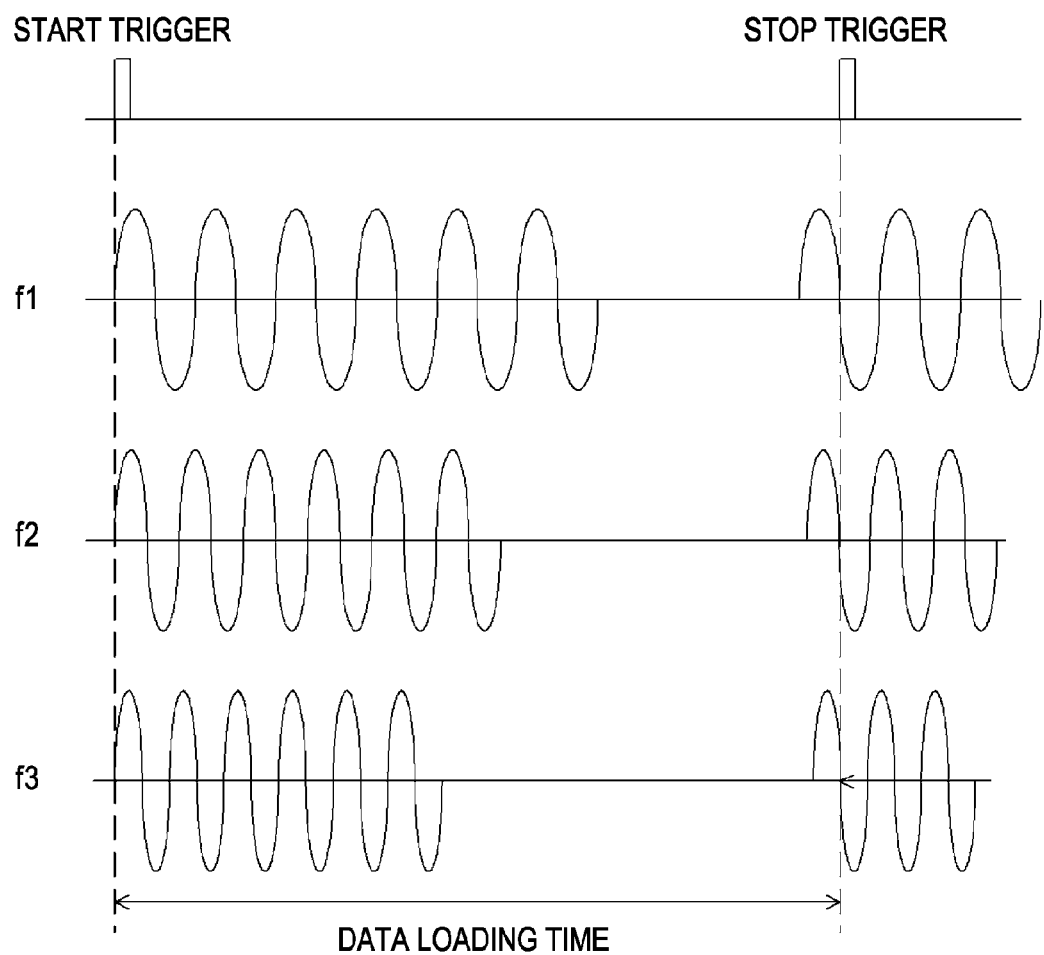
FIG. 4 is a diagram illustrating a relationship among data loaded as signal in by a start trigger and a stop trigger.

FIG. 4 illustrates a relationship between reference signals output from the BPFs 52a to 52c and data loaded as signal in by a start trigger and a stop trigger. The signals corresponding to three kinds of light having wavelengths of 2.1 μm (f1), 1.94 μm (f2), and 1.7 μm (f3), respectively, are loaded simultaneously and input to the lock-in amplifiers 59a to 59c.

Note that the start trigger and the stop trigger are, for example, oscillated by the divider 60 arranged between the signal generator 51 and the ADC 58. The divider 60 oscillates the start/stop trigger per 100 pulses, for example.

As described above, the present measurement apparatus includes the lock-in amplifiers 59a to 59c corresponding to all channels to detect signals from all the channels. The lock-in amplifiers 59a to 59c respectively receive detected signals output from the light detecting element 56 (detector) and reference signals (modulation signals for modulating light sources at different frequencies). As a result, the frequencies of the detected signal including the whole (or part) of the signal information from each of the light sources 54a to 54c are discriminated by each of the lock-in amplifiers 59a to 59c to result in a discriminated signal, which is then output from each lock-in amplifier.

As described above, the A/D converter 58 has the function of, with reference to time, matching the duration of a loaded waveform with an integral multiple of the period of the initial signal output from the signal generator 51. The A/D converter 58 also has a function of, with reference to frequency, matching the width of a time window to load the detected signal with an integral multiple of an inverse of the frequency of the modulation signal (reference signal).

With these functions, the present measurement apparatus can cause the three frequency components of the detected signal input to each of the lock-in amplifiers 59a to 59c to have the orthogonal relationship with each other. Despite the finite measurement time, therefore, the three frequency components are discriminated without being mixed with each other. This makes it possible to obtain a high signal-to-noise ratio.

In the present measurement apparatus, the output signal from the signal generator 51 contains frequency components other than the target frequencies. Before the signal reaches the light source driving amplifiers 53a to 53c, therefore, only the target frequencies are extracted by the bandpass filters 52a to 52c. At this time, a bandpass filter having good frequency characteristics may as well be used so as not for the frequencies of the signals to overlap.

In addition, harmonic distortion of the amplifier may cause mutual interference between the signals. Assume, for example, that the magnitude of the harmonic distortion with respect to a certain main signal is 0.01%. In this case, a harmonic signal is output with a magnitude of 0.01% of the main signal. For example, therefore, frequencies of harmonics of a signal having a frequency f are $2f, 3f, 4f, \ldots$. If these frequencies are the same as frequencies of a main signal from another channel, noise will be contained in the another channel. In this case, the figures concerning distortion are determined depending on the degree of precision required. Therefore, the harmonic distortion of the light source driving amplifiers 53a to 53c and the current/voltage converter 57 may be of, for example, a magnitude of 0.0001% or less.

Note that the present measurement apparatus described above is merely a certain example.

Figure 5:
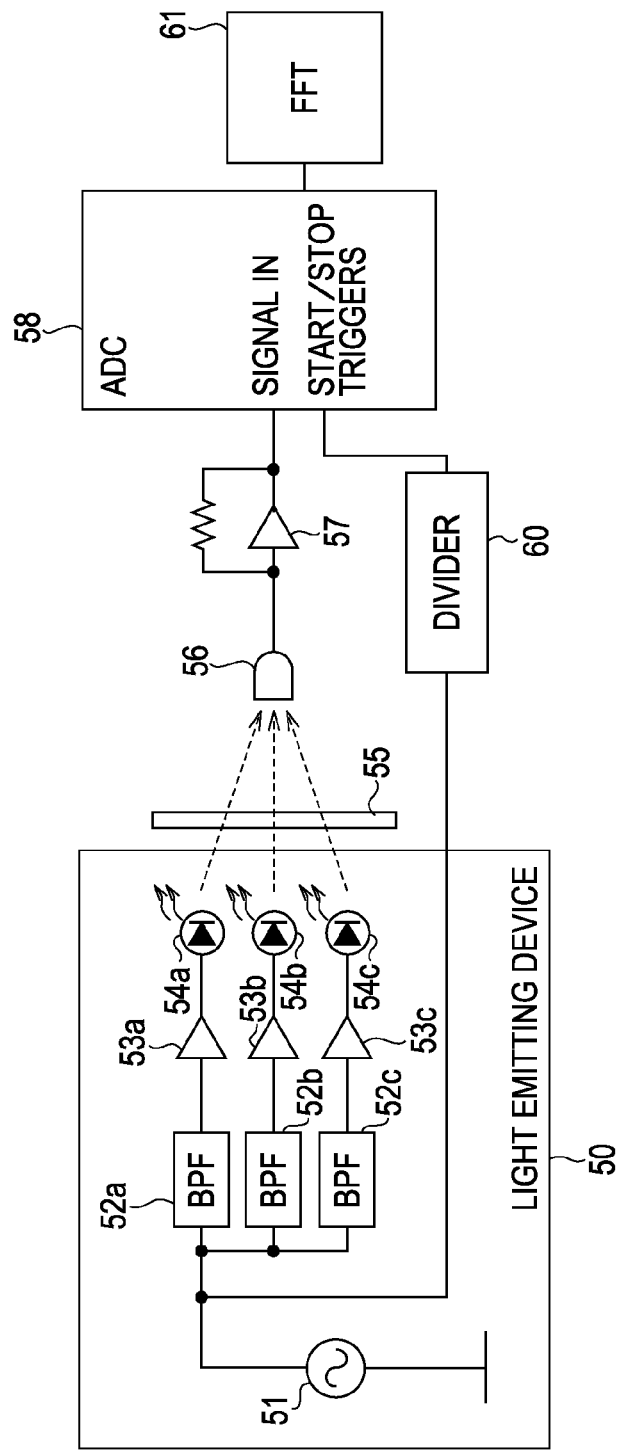
FIG. 5 is a block configuration diagram illustrating another embodiment of the multichannel photometric measurement apparatus.
Figure 6A:
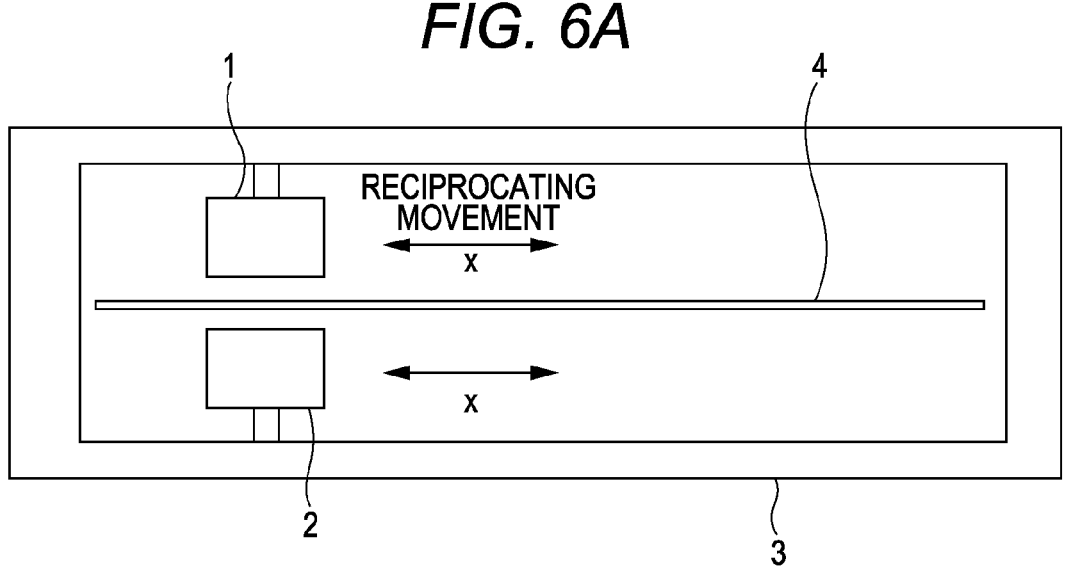
FIG. 6A is a configuration diagram illustrating main parts of the apparatus in the related art.
Figure 6B:
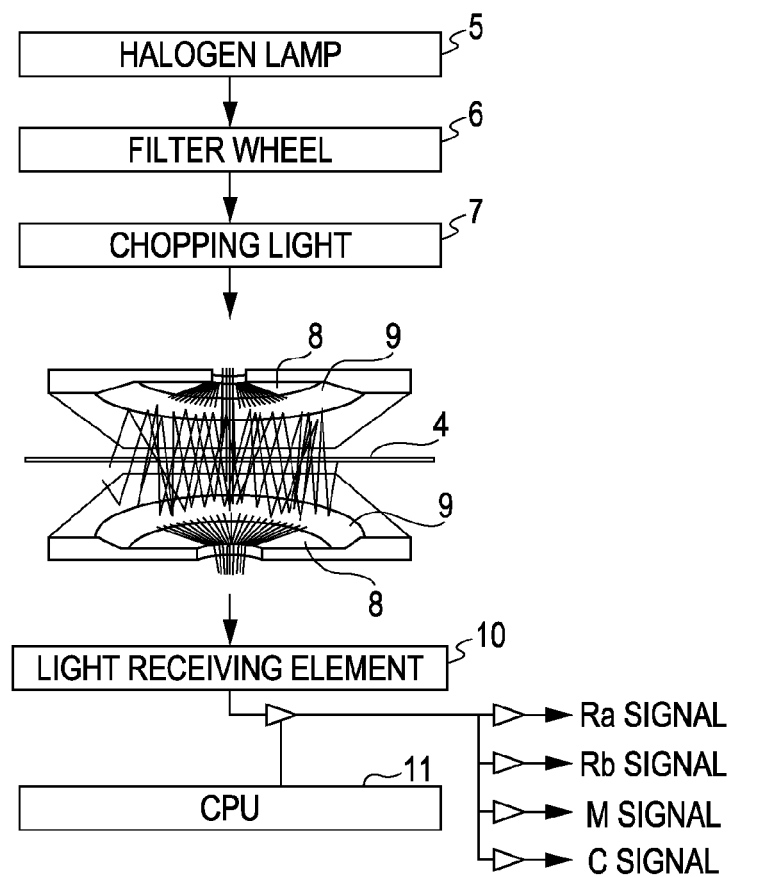
FIG. 6B is a configuration diagram illustrating the main parts, i.e., an upper sensor head and a lower sensor head in detail.
Figure 7:
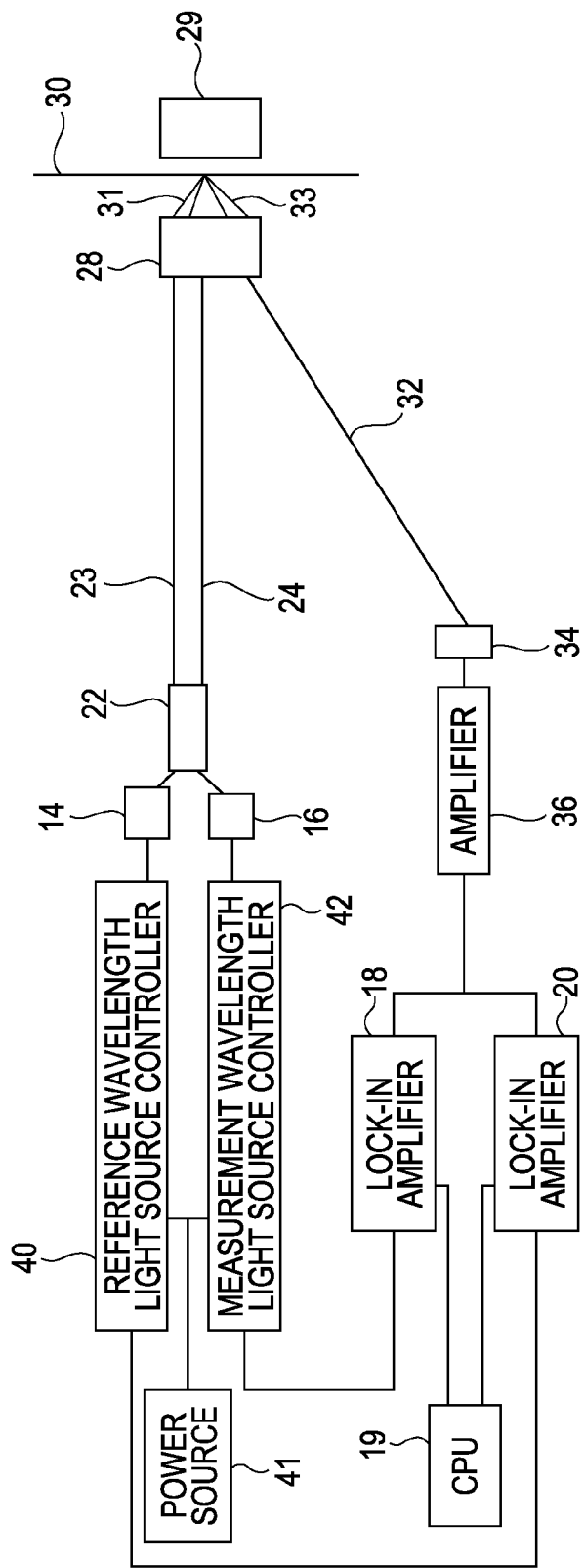
FIG. 7 is a block configuration diagram illustrating another example of the related art.

For example, the present measurement apparatus illustrated in FIG. 1 processes the digital detected signal by lock-in detection. Alternatively, however, the detected signal may be processed by discrete Fourier transform. FIG. 5 is a block configuration diagram illustrating another configuration example of the present measurement apparatus. In the present measurement apparatus illustrated in FIG. 5, a discrete Fourier transform (FFT) device 61 (hereinafter referred to as "FFT 61") is arranged at a later stage of the ADC 58. The FFT 61 filters a digital detected signal per frequency domain.

The detected signal having three frequency components has a wavelength of one-integer-th (one over an integral multiple) of data duration. Therefore, the intensities (energy) of the signal are aggregated to a specific term by discrete Fourier transform. The FFT 61 extracts the specific term while blocking the other terms by filtering. With this operation, the three frequency components are discriminated without being mixed with each other. This makes it possible to obtain a high signal-to-noise ratio. In addition, the configuration employing the FFT 61 makes it easy to process the signals compared to the configuration employing lock-in amplifiers.

In the present embodiment, the rectangular wave generated by the signal generator 51 has a duty ratio of 50%. However, the waveforms generated by the signal generator 51 do not have to have a duty ratio of 50%, as long as the waveforms are aggregated to a specific term according to the frequencies by discrete Fourier transform. Also, the waveform generated by the signal generator 51 is not limited to a rectangular wave but may be a triangular wave or a sawtooth wave, for example.

The reference signals input to the lock-in amplifiers 59a to 59c do not have to be signals generated from the rectangular wave and having a specific frequency. For example, a plurality of monochrome signals corresponding to all the frequency components contained in the rectangular wave may be used as the reference signals.

The initial signals containing harmonics and input to the BPFs 52a to 52c may be output from the same signal generator 51. With this configuration, the orthogonality among the modulation signals output from the BPFs 52a to 52c can be maintained. Therefore, the initial signal output from the single signal generator may be divided according to the number of BPFs. By passing the signal containing harmonics through the BPF, it is possible to extract a signal having a single frequency.

The present embodiment describes, as an example, the measurement apparatus for calculating the moisture percentage or thickness of paper (sheet). However, this measurement apparatus can be applied to a multichannel photometric measurement apparatus which can be used to measure various samples besides paper.

The light emitting device 50 can also be expressed as a light emitting device including a light source driving device adapted to be modulated at different frequencies and a plurality of light sources adapted to select the plurality of frequencies generated by the frequency generator and to be driven by the selected frequencies.

It is also possible to say that, in the present measurement apparatus, the light sources are driven by different frequencies having the orthogonal relationship. The rectangular wave output from the signal generator 51 may have such waveforms as to be aggregated to a plurality of specific terms according to frequency. The reference signals used in the lock-in amplifiers may carry different frequencies that are similarly different on the side of the detector with reference to the rectangular wave.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A multichannel photometric measurement apparatus, comprising:

a single signal generator for generating an initial signal, the initial signal containing a harmonic component for collectively generating a plurality of modulation signals;

a light emitting device including a plurality of light sources that are respectively drivable by each of the plurality of modulation signals having different frequencies;

a light detector for detecting a plurality of kinds of light emitted from the light emitting device; and discriminating means for discriminating a detected signal output from the light detector per frequency domain of each of the different frequencies for each of the modulation signals, wherein the signal generator is included in the light emitting device, wherein the light emitting device further includes a plurality of bandpass filters that extract a predetermined different frequency component from the initial signal generated by the signal generator, and wherein the plurality of light sources is each drivable by a modulation signal having the frequency component extracted by a corresponding one of the bandpass filters.

2. The multichannel photometric measurement apparatus according to claim 1, wherein each of the plurality of bandpass filters has a cutoff characteristic to respectively extract the predetermined different frequency component from the initial signal generated by the signal generator.

3. A multichannel photometric measurement apparatus, comprising:

a single signal generator for generating an initial signal, the initial signal containing a harmonic component for collectively generating a plurality of modulation signals;

a light emitting device including a plurality of light sources that are respectively drivable by each of the plurality of modulation signals having different frequencies;

a light detector for detecting a plurality of kinds of light emitted from the light emitting device; and discriminating means for discriminating a detected signal output from the light detector per frequency domain of each of the different frequencies for each of the modulation signals, wherein the discriminating means includes an A/D converter that matches a width of a time window to load the detected signal with an integral multiple of an inverse of the frequency of the modulation signal to cause a plurality of frequency components contained in the detected signal input to the discriminating means to have an orthogonal relationship with each other.

* * * * *